United States Patent
Neymeyr

Patent Number: 6,058,824
Date of Patent: *May 9, 2000

[54] CUTTER HOLDER FOR ACCOMMODATING WEDGE-SHAPED MICROTOME CUTTERS

[75] Inventor: Ulrich Neymeyr, Heidelberg, Germany

[73] Assignee: Leica Instruments GmbH, Nussloch, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/921,663

[22] Filed: Sep. 2, 1997

[30] Foreign Application Priority Data

Sep. 2, 1996 [DE] Germany ............... 196 35 538

[51] Int. Cl.$^7$ .................................................. G01N 1/06
[52] U.S. Cl. ............................ 83/698.21; 83/698.51; 83/856; 83/915.5
[58] Field of Search ............. 83/698.11, 698.21, 83/699.11, 699.51, 699.61, 856, 915.5, 698.31, 703, 707, 713

[56] References Cited

U.S. PATENT DOCUMENTS

| | | | |
|---|---|---|---|
| 3,190,164 | 6/1965 | McCormick | 83/915.5 X |
| 3,191,476 | 6/1965 | McCormick | 83/915.5 X |
| 3,296,821 | 1/1967 | Malinin | 83/915.5 X |
| 3,599,523 | 8/1971 | Pickett | 83/915.5 X |
| 4,262,567 | 4/1981 | Bettin | 83/915.5 X |
| 4,472,989 | 9/1984 | Endo | 83/915.5 X |
| 4,690,023 | 9/1987 | Berleth et al. | 83/699.61 |
| 4,700,600 | 10/1987 | Pickett | 83/915.5 X |
| 5,148,729 | 9/1992 | Krumdieck | 83/915.5 X |
| 5,535,654 | 7/1996 | Niesporek et al. | 83/915.5 X |
| 5,669,278 | 9/1997 | Metzner | 83/165 |

FOREIGN PATENT DOCUMENTS

| | | |
|---|---|---|
| 2143 529 | 3/1973 | Germany . |
| 3413 251 | 2/1985 | Germany . |
| 195 06 837 | 7/1996 | Germany . |

*Primary Examiner*—Clark F. Dexter
*Attorney, Agent, or Firm*—Foley & Lardner

[57] ABSTRACT

A a cutter holder (1) for wedge-shaped microtome cutters (5), in particular of regrindable hard-metal or steel cutters or wedge-shaped blade holders, in the case of which a clamping jaw (2) is mounted pivotably on a base (4) for the purpose of setting he clearance angle of the microtome cutter (5). The cutter holder (1) has a single clamping jaw (2) which is open at the front and has a centrally arranged setscrew (6) for accommodating the microtome cutter (5). A thrust piece (8) is arranged between the microtome cutter (5) and the clamping jaw (2). The thrust piece (8) is connected in a nonpositive manner to the setscrew (6) for the purpose of clamping the microtome cutter (5). In the region of the cutting blade (5), the thrust piece (8) is equipped with a profile (9) of U-shaped design, so that the clamping force of the setscrew (6) is transmitted to two points of the microtome cutter (5).

19 Claims, 2 Drawing Sheets

CUTTER HOLDER FOR ACCOMMODATING WEDGE-SHAPED MICROTOME CUTTERS

FIELD OF THE INVENTION

This invention relates to a cutter holder for accommodating wedge-shaped microtome cutters, in particular, regrindable hard-metal, steel cutters, or wedge shaped blade holders.

BACKGROUND OF THE INVENTION

Wedge-shaped cutting blades made of hard metal or steel are used over a relatively long period of time and, by contrast to simple disposal blades, can be reground. Owing to their geometry, these wedge-shaped cutting blades are extremely stable, so that they can be used in a cutter holder of simple construction. To this end, cutter holders are known which have a right-hand and a left-hand clamping jaw.

The cutter is fixed in the clamping jaws by means of two screws, which each act on the back face of the cutter.

Holders of wedge-shaped design are known for accommodating blade-like cutters (disposal blades), into which holders these blades are clamped. Depending on the application, these blade holders are also used instead of a wedge-shaped cutting blade, here again the holder being fixed in the two clamping jaws.

To align the cutting blade with the object to be cut, the cutter holder is pivotably mounted on a base. A cutter holder of this kind is illustrated and described, for example, in DE 21 43 529.

A drawback of these known cutter holders is the fact that the two clamping jaws, for reasons of stability, are of upwardly closed design and thus the cutting blade can only be slid into the corresponding guide with difficulty.

A cutter holder of multipart design, which in addition to two closed supports has a continuous abutment device, is known from DE 34 13 251. One of the back faces of the cutter is supported against this abutment device. The cutting blade is clamped by means of a continuous clamping jaw, which is actuated by means of an eccentric and acts on the other rear face of the cutter.

This cutter holder provides a high level of stability in the cutting region of the cutter. However, it is necessary to take into account the fact that the cut samples slide onto the clamping jaw and can thus only be removed with difficulty.

A cutter holder for accommodating wedge-shaped microtome cutters which has two upwardly open clamping jaws for accommodating the cutting blade is known from DE 195 06 837 C1. A setscrew is provided in each clamping jaw for the purpose of fixing the cutting blade in the cutter holder, these setscrews being connected to a continuous clamping plate. When screwing in the two setscrews, the clamping plate is pressed against the back face of the cutter and the cutting blade is fixed in the cutter holder.

A cutter holder of this kind has proven itself in practice and is distinguished by high mechanical stability in the cutting region. In addition, the cutter holder allows simple removal of the cut sample from the back face of the cutter.

When cutting the sample, only a small part of the cutter blade is used, so that after this part has been worn away the cutting blade is displaced within the cutter holder. To do this, it is necessary to loosen the two setscrews and to displace the cutting blade by a specific amount. It is necessary to ensure here that neither the angular position of the cutting blade with respect to the object nor the distance of the cutter blade from the object changes. This cutter holder allows the cutting blade to be displaced within the cutter holder while maintaining the set position of the cutter. However, in practice it has been found that operating two setscrews makes it difficult to displace the cutting blade.

SUMMARY OF THE INVENTION

The object of the present invention is to develop a cutter holder of the type described above in reference to DE 195 06 837, but in such a manner that manipulating the cutter holder when changing a cutter or its orientation is simplified while maintaining the high mechanical stability.

This object is achieved according to the invention by means of a cutter holder for wedge-shaped microtome cutters comprising: a single clamping jaw with an open front portion and a centrally arranged setscrew for accommodating a microtome cutter; a thrust piece arranged between the microtome cutter and the clamping jaw, the thrust piece being connected in a nonpositive manner to the setscrew so as to clamp the microtome cutter, wherein the thrust piece includes a U-shaped portion and two lugs arranged parallel to a blade portion of the microtome cutter, the U-shaped portion extending parallel to the blade portion of the microtome cutter, whereby the setscrew exerts a clamping force centrally on the thrust piece which is transmitted to the cutter via the two lugs.

According to a feature of the invention, the clamping jaw includes a continuous screw thread for accommodating the setscrew.

According to another feature of the invention, the thrust piece includes a recess in a region of a side which is oriented towards the clamping jaw.

According to stall another feature of the invention, the thrust piece is connected to the clamping jaw via a compression spring.

According to yet another feature of the invention, a magnet is arranged in the cutter holder as a support for a rear narrow :ace of the cutter which is situated opposite to the cutter blade.

The invention makes it possible to use a simply equipped cutter holder having only a single, open clamping jaw for wedge-shaped cutting blades or wedge-shaped blade holders with a high level of stability.

It has proven advantageous to use a cutter holder of this kind in traversing microtomes, since the cutting blade is freely accessible in the active cutting region and there are thus no problems with removing the sections. Due to the clamping with only a single, manually actuable element, the cutter can be exchanged or displaced within the cutter holder quickly and precisely, the U-shaped configuration of the thrust piece meaning that the clamping force is transmitted to two points on the back face of the cutter, thus resulting in reliable clamping of the cutting blade.

Owing to the arrangement of a magnet in the cutter holder, the cutting blade is fixed against unintended displacement and head in a defined position when the setscrew is loosened.

BRIEF DESCRIPTION OF THE DRAWINGS

The invention is explained in more detail with reference to an exemplary embodiment with the aid of the diagrammatic drawings, in which.

DETAILED DESCRIPTION OF THE PREFERRED EMBODIMENTS

Figure 1:
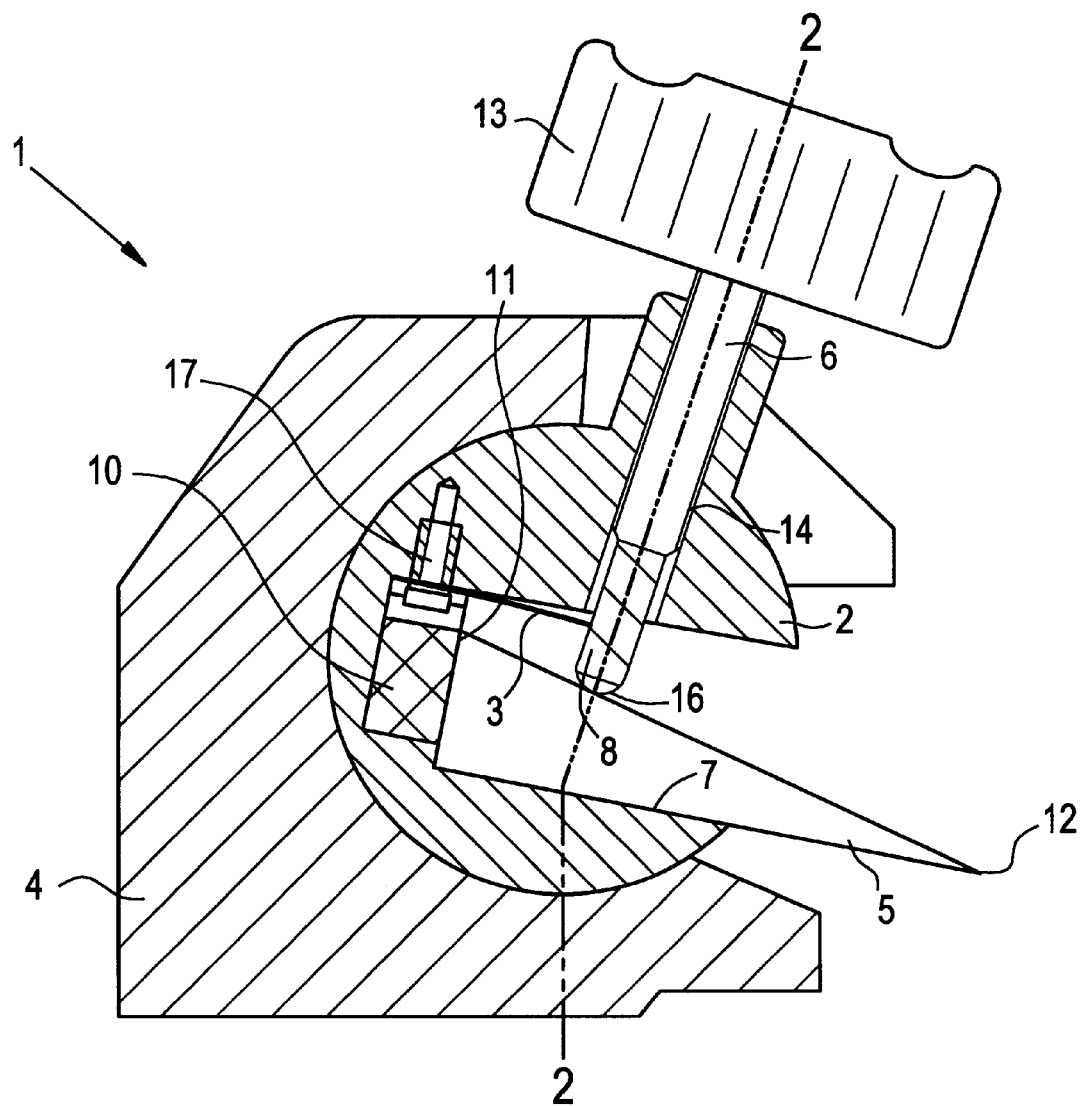
FIG. 1 shows a section, illustrated from the side, through the cutter holder with integrated clamping jaw.

FIG. 1 shows a cutter holder 1 which includes a base 4 with a clamping jaw 2 and a clamped-in wedge-shaped clamping jaw 2. The cutter is mounted pivotably on the base 4, for the purpose of setting the clearance angle of the cutter or of aligning it with respect: to an object, a locking means (not shown) fixing the respectively set clearance angle.

A setscrew 6 with an actuating handle 13 is guided through the clamping jaw 2 via a screw thread 14 and presses against a thrust Niece 8 by means of its end situated opposite to the actuating handle 13. The profile of the thrust piece 8 is U-shaped and has two lugs 16. The cutter 5 is clamped in the clamping jaw 2, between the two adjacently arranged lugs 16 and a cutter bottom support 7, the cutter rear narrow face 11 situated opposite to the cutting edge 12 of the cutter 5 and 12 bearing against a magnet 10. In the example shown in FIGS. 1 and 2, the bottom support 7 is defined by a part of the open front portion of the clamping jaw 2. The magnet 10 brings about a defined position of the cutter 5 on being aligned in the cutter holder 1.

The thrust piece 8 is connected in a nonpositive manner to a compression spring 3, which via a fastening screw 17 is fastened to the clamping jaw 2. The compression spring 3 holds the thrust piece 8 in position when exchanging the microtome cutter 5.

Figure 2:
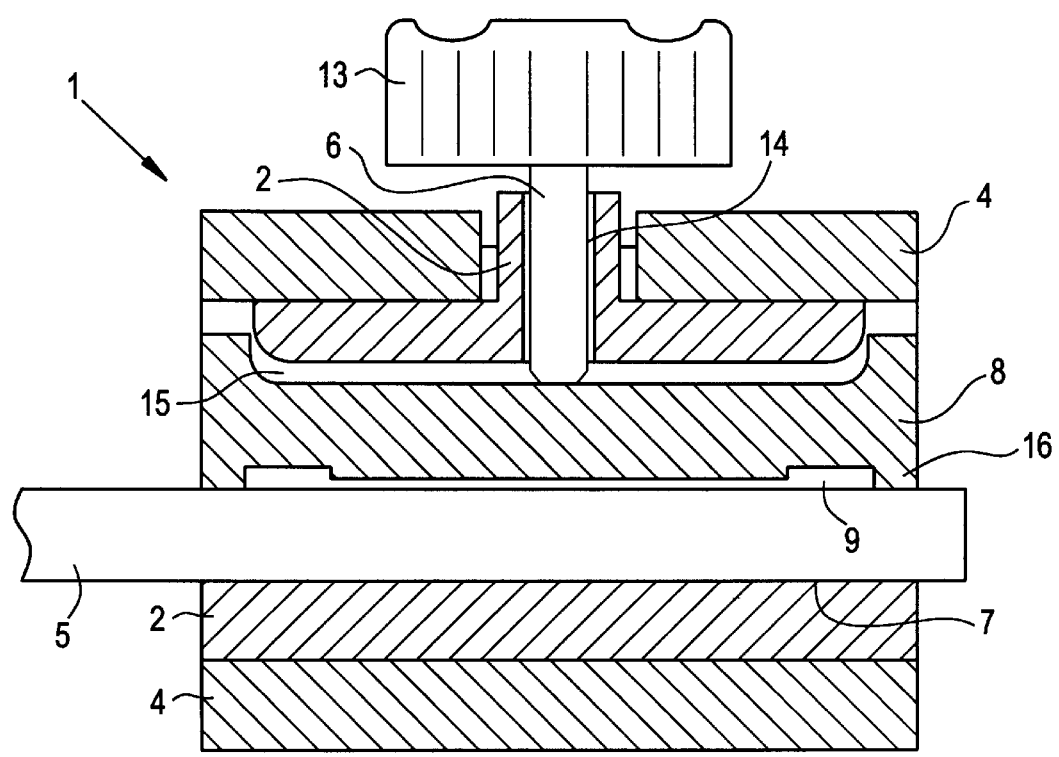
FIG. 2 shows a section through the cutter holder on line A—A from FIG. 1.

FIG. 2 shows a section through the cutter holder 1 on line A—A from FIG. 1. The thrust piece 8 has a recess 15, in which the clamping jaw 2 engages. This arrangement prevents lateral displacement of the thrust piece 8 with respect to the clamping jaw 2 when screwing in the setscrew 6. The free end of the setscrew 6 presses against the thrust piece 8. This pressure is transmitted via the U-shaped profile 9 and the two lugs 16, which are arranged parallel next to one another, to the back of the cutter 5. The other side of the back of the cutter is here supported against the cutter bottom support 7.

The subject matter of the invention means that only a single setscrew 6 has to be actuated to fix the cutter 5 in the cutter holder 1. In the case of cutter holders with two setscrews, the actuating handles have to be selected to be small, for space reasons, as a result of which it is more difficult for the operator to apply the torque. In addition to the advantage of there being only one setscrew, the subject matter of the present invention thus also exhibits improved ergonomics.

The resultant dimensioning of the cutter holder 1 allows a large range of displacement of the cutter 5 within the cutter holder 1 and thus permits optimum utilization of the cutter 5. Due to the small structural size, a cutter holder of this kind may advantageously be used for traversing microtomes. The currently active cutting region of the cutter in this case lies outside the cutter holder, so that simple and unimpeded removal of the sections from the back of the cutter is possible.

It is within the scope of the invention to replace the wedge-shaped cutting blade described in the exemplary embodiment with a blade holder of wedge-shaped design for thin blades, this holder being known per se.

Specific embodiments have now been described to illustrate, but not to limit the invention. Various modifications will be apparent to those skilled in the art. Such modifications are intended to be within the scope of the invention as defined in the appended claims.

What is claimed is:

1. A cutter assembly comprising:
   a microtome cutter implement;
   a base having only a single clamping jaw mounted thereon, the single clamping jaw having an open front portion;
   a single setscrew having a portion thereof disposed within the clamping jaw; and
   a thrust piece arranged between the microtome cutter implement and the clamping jaw, the setscrew disposed against the thrust piece, clamping the thrust piece against the microtome cutter implement;
   wherein the thrust piece includes a U-shaped portion and two lugs arranged parallel to a back portion of the microtome cutter implement, the U-shaped portion extending parallel to the back portion of the microtome cutter implement; and
   wherein the setscrew is disposed proximate a central portion of the thrust piece, whereby the setscrew exerts a clamping force centrally on the thrust piece which is transmitted substantially uniformly to the microtome cutter implement via the two lugs.

2. The cutter assembly as claimed in claim 1, wherein the clamping jaw includes a continuous screw thread accommodating the setscrew.

3. The cutter assembly of claim 2, wherein the thrust piece includes a recess in a region of a side thereof which is oriented towards the clamping saw.

4. The cutter assembly of claim 3, wherein the thrust piece is connected to the clamming jaw via a compression spring.

5. The cutter assembly of claim 2, further comprising a magnet disposed within the clamping jaw and supports a rear narrow face of the microtome cutter implement, said rear narrow face being situated opposite to a cutting edge on the microtome cutter implement.

6. The cutter assembly of claim 1, wherein the thrust piece includes a recess in a region of a side which is oriented towards the clamping jaw.

7. The cutter assembly of claim 6, wherein the thrust piece is connected to the clamping jaw via a compression spring.

8. The cutter assembly of claim 7, further comprising a magnet disposed within the clamping jaw and supports a rear narrow face of the microtome cutter implement, said rear narrow face being situated opposite to a cutting edge on the microtome cutter implement.

9. The cutter assembly of claim 6, further comprising a magnet disposed within the clamping jaw and supports a rear narrow face of the microtome cutter implement, said rear narrow face being situated opposite to a cutting edge on the microtome cutter implement.

10. The cutter assembly of claim 1, further comprising a magnet disposed within the clamping jaw and supports a rear narrow face of the microtome cutter implement, the rear narrow face being situated opposite to a cutting edge on the microtome cutter implement.

11. The cutter assembly of claim 1, wherein the microtome cutter implement is a regrindable hard-metal cutter.

12. The assembly holder of claim 1, wherein the microtome cutter implement is a steel cutter.

13. The cutter assembly of claim 1, wherein the microtome cutter implement is wedge-shaped.

14. The cutter assembly of claim 1, wherein the clamping jaw is mounted pivotably on the base, whereby the clearance angle of the microtome cutter implement is adjustable.

15. A cutter holder for accommodating a microtome cutter implement comprising:

a base having only a single clamping jaw mounted thereon, the single clamping jaw having an open front portion;

a single setscrew having a portion thereof disposed within the clamping jaw;

a bottom support defined by a part of the open front portion of the clamping jaw; and a thrust piece disposed within the open front portion of the clamping jaw, the thrust piece having a top portion and a bottom portion disposed over the bottom support, wherein the bottom portion of the thrust piece includes a U-shaped portion and two lugs arranged parallel to the bottom support;

whereby, when the microtome cutter implement is accommodated between the thrust piece and the bottom support, the setscrew is movable to thereby exert a clamping force against a central portion of the top portion of the thrust piece which is transmitted substantially uniformly to the microtome cutter implement via the two lugs.

16. The cutter holder of claim 15, wherein the clamping jaw includes a continuous screw thread accommodating the setscrew.

17. The cutter holder of claim 15, wherein the thrust piece includes a recess in the top portion of the thrust piece.

18. The cutter holder of claim 15, wherein the thrust piece is connected to the clamping jaw via a compression spring.

19. The cutter holder of claim 15, further comprising a magnet disposed over the bottom support, whereby the magnet supports a rear narrow face of the microtome cutter implement accommodated within the clamping jaw.

* * * * *